(12) United States Patent
Chen et al.

(10) Patent No.: US 11,384,350 B2
(45) Date of Patent: Jul. 12, 2022

(54) CYTOTOXIC MOLECULES RESPONSIVE TO INTRACELLULAR LIGANDS FOR SELECTIVE T CELL MEDIATED KILLING

(71) Applicant: THE REGENTS OF THE UNIVERSITY OF CALIFORNIA, Oakland, CA (US)

(72) Inventors: Yvonne Y. Chen, Los Angeles, CA (US); Patrick Ho, Fremont, CA (US)

(73) Assignee: The Regents of the University of California, Oakland, CA (US)

(*) Notice: Subject to any disclaimer, the term of this patent is extended or adjusted under 35 U.S.C. 154(b) by 1080 days.

(21) Appl. No.: 15/536,009

(22) PCT Filed: Dec. 14, 2015

(86) PCT No.: PCT/US2015/065623
§ 371 (c)(1),
(2) Date: Jun. 14, 2017

(87) PCT Pub. No.: WO2016/100233
PCT Pub. Date: Jun. 23, 2016

(65) Prior Publication Data
US 2017/0362582 A1 Dec. 21, 2017

Related U.S. Application Data

(60) Provisional application No. 62/091,937, filed on Dec. 15, 2014.

(51) Int. Cl.
| | | |
|---|---|---|
| C12N 9/64 | (2006.01) | |
| A61K 35/17 | (2015.01) | |
| C12N 15/85 | (2006.01) | |
| C07K 14/47 | (2006.01) | |
| A61K 38/48 | (2006.01) | |
| C07K 16/40 | (2006.01) | |
| C12N 5/0783 | (2010.01) | |

(52) U.S. Cl.
CPC ............ *C12N 9/6467* (2013.01); *A61K 35/17* (2013.01); *A61K 38/482* (2013.01); *C07K 14/47* (2013.01); *C07K 14/4702* (2013.01); *C07K 16/40* (2013.01); *C12N 5/0636* (2013.01); *C12N 9/64* (2013.01); *C12N 15/85* (2013.01); *C12Y 304/21079* (2013.01); *C07K 2317/622* (2013.01); *C07K 2319/00* (2013.01); *C07K 2319/95* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,797,368 | A | 1/1989 | Carter et al. |
| 5,138,941 | A | 8/1992 | Strauss |
| 5,139,941 | A | 8/1992 | Muzyczka |
| 5,670,373 | A | 9/1997 | Kishimoto |
| 5,821,337 | A | 10/1998 | Carter et al. |
| 6,319,494 | B1 | 11/2001 | Capon et al. |
| 7,151,169 | B2 | 12/2006 | Thompson et al. |
| 7,276,477 | B2 | 10/2007 | Osslund et al. |
| 7,479,543 | B2 | 1/2009 | Tsuchiya et al. |
| 7,741,465 | B1 | 6/2010 | Eshhar et al. |
| 8,012,482 | B2 | 9/2011 | Adams et al. |
| 8,063,182 | B1 | 11/2011 | Brockhaus et al. |
| 8,236,541 | B2 | 8/2012 | Black |
| 8,399,645 | B2 | 3/2013 | Campana et al. |
| 8,580,264 | B2 | 11/2013 | Zhang et al. |
| 9,447,194 | B2 | 9/2016 | Jensen |
| 9,464,140 | B2 | 10/2016 | June et al. |
| 9,518,123 | B2 | 12/2016 | June et al. |
| 9,540,445 | B2 | 1/2017 | June et al. |
| 9,834,590 | B2 | 12/2017 | Campana et al. |
| 2004/0026871 | A1 | 2/2004 | Stephens et al. |
| 2004/0254774 | A1* | 12/2004 | Loh .......................... C12N 9/22 703/11 |

(Continued)

FOREIGN PATENT DOCUMENTS

| | | |
|---|---|---|
| EP | 1810980 | 7/2007 |
| EP | 2330193 | 6/2011 |

(Continued)

OTHER PUBLICATIONS

Dalken, et al., "Targeted Induction of Apoptosis by Chimeric Granzyme B Fusion Proteins Carrying Antibody and Growth Factor Domains for Cell Recognition," *Cell Death Differentiation*, 13, pp. 576-585. (2006).

Duebner, et al., "Reprogramming Control of an Allosteric Signaling Switch Through Modular Recombination," *Science*, 301(5641), pp. 1904-1908. (2003).

Extended European Search Report Issued in Corresponding European Application 15870819.8, dated Apr. 13, 2018.

Ho, et al., "Covert Cancer Therapeutics: Engineering T Cells to Interrogate Intracellular Tumor Antigens," 2015 AIChE Annual Meeting, Nov. 12, 2015, Salt Lake City, UT.

(Continued)

*Primary Examiner* — Kagnew H Gebreyesus
(74) *Attorney, Agent, or Firm* — Norton Rose Fulbright US LLP

(57) ABSTRACT

Compositions and methods are provided for the cell-mediated targeted killing of diseased cells based on the presence of an intracellular antigen, rather than a surface-bound marker. The targeting cells are modified to express a cytotoxic protein that is delivered into a targeted cell, and after delivery is selectively activated by the presence of a cytoplasmic protein of interest. In one embodiment of the invention, the cytotoxic molecule is a Granzyme B (GrB) polypeptide. In the compositions of the invention, GrB is modified to render its cytotoxic enzymatic functions inactive, until the presence of an intracellular antigen unlocks the GrB molecule to enable enzymatic activities.

12 Claims, 11 Drawing Sheets

Figure 1:
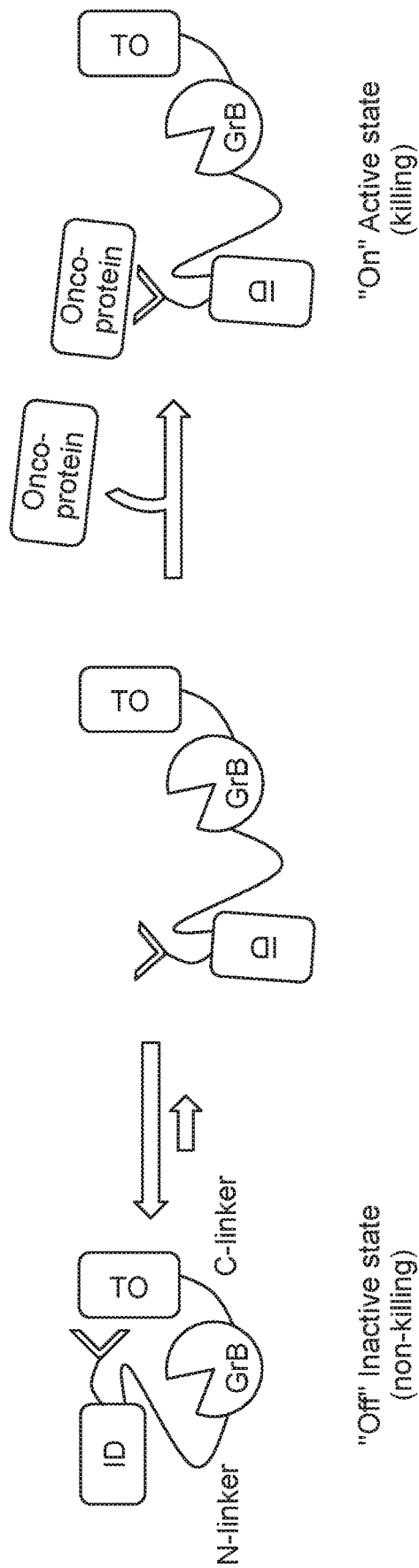

Specification includes a Sequence Listing.

(56) References Cited

U.S. PATENT DOCUMENTS

| | | |
|---|---|---|
| 2006/0135517 A1 | 6/2006 | Lee et al. |
| 2006/0251658 A1 | 11/2006 | Ledbetter et al. |
| 2007/0142376 A1 | 6/2007 | Fleenor et al. |
| 2009/0068158 A1 | 3/2009 | Medin et al. |
| 2010/0330676 A1 | 12/2010 | Horowitz et al. |
| 2011/0008364 A1 | 1/2011 | Ledbetter et al. |
| 2011/0286980 A1 | 11/2011 | Brenner et al. |
| 2013/0071414 A1 | 3/2013 | Dotti et al. |
| 2013/0280220 A1 | 10/2013 | Ahmed et al. |
| 2014/0141000 A1 | 5/2014 | Chiu et al. |
| 2014/0314760 A1 | 10/2014 | Rosenblum et al. |
| 2015/0038684 A1 | 2/2015 | Jensen |
| 2017/0333480 A1 | 11/2017 | Cooper et al. |
| 2017/0342144 A1 | 11/2017 | Wei et al. |
| 2017/0362582 A1 | 12/2017 | Chen et al. |
| 2017/0368098 A1 | 12/2017 | Chen et al. |
| 2018/0022815 A1 | 1/2018 | Chang |

FOREIGN PATENT DOCUMENTS

| | | |
|---|---|---|
| EP | 3550020 | 10/2019 |
| JP | 2003-501348 | 1/2003 |
| JP | 2007-515949 | 6/2007 |
| JP | 2008-529503 | 8/2008 |
| JP | 2013-542179 | 11/2013 |
| JP | 2015-513394 | 5/2015 |
| WO | WO 1992/019759 | 11/1992 |
| WO | WO 1994/012520 | 6/1994 |
| WO | WO 98/50432 | 11/1998 |
| WO | WO 2004/019990 | 3/2004 |
| WO | WO 2005/097832 | 10/2005 |
| WO | WO 2006/046661 | 5/2006 |
| WO | WO 2011/140170 | 11/2011 |
| WO | WO 2013/123061 | 8/2013 |
| WO | WO 2014/072233 | 5/2014 |
| WO | WO 2014/164709 | 10/2014 |
| WO | WO 2014/172584 | 10/2014 |
| WO | WO 2015/121454 | 8/2015 |
| WO | WO 2016/094304 | 6/2016 |
| WO | WO 2017/075433 | 5/2017 |
| WO | WO 2017/096329 | 6/2017 |
| WO | WO 2017/172981 | 10/2017 |
| WO | WO 2018/103502 | 6/2018 |

OTHER PUBLICATIONS

Ho, et al., "Modularly Constructed Synthetic Granzyme B Molecule Enables Interrogation of Intracellular Proteases for Targeted Cytotoxicity," ACS Synthetic Biology, 6, pp. 1484-1495. (2017).
International Search Report and Written Opinion Issued in Corresponding PCT Application No. PCT/US2015/065623, dated Apr. 19, 2016.
Malakhov, et al., SUMO Fusions and SUMO-Specific Protease for Efficient Expression and Purification of Proteins, *Journal of Structural and Functional Genomics*, 5(1-2). (2004).
Pastan, et al., "Immunotoxin Treatment of Cancer," Annual Review of Medicine, 58, pp. 221-237. (2007).
Stahnke, et al., "Granzyme B-H22 (scFV), a Human Immunotoxin Targeting CD64 in Acute Myeloid Leukemia in Monocytic Subtypes," *Molecular Cancer Therapeutics*, 7(9), pp. 2924-2932. (2008).
Wyatt, et al., "Human Telomerase Reverse Transcriptase (hTERT) Q169 is Essential for Telomerase Function In Vitro and In Vivo," *PLoS One*, 4(9), pp. 1-14. (2009).
Zhao, et al., "Secreted Antibody/Granzyme B Fusion Protein Stimulates Selective Killing of HER2-Overexpressing Tumor Cells," *The Journal of Biological Chemistry*, 279(20), pp. 21343-21348. (2004).
Bond, J.S. et al., "Intracellular Proteases," *Annual Review of Biochemistry*, 56: 333-364, 1987.
Duffy, M.J., "Proteases as Prognostic Markers in Cancer," *Clinical Cancer Research*, 2: 613-618, 1996.
Chen, et al., " A Unique Substrate Recognition Profile for Matrix Metalloproteinase-2," *The Journal of Biological Chemistry*, 277(6): 4485-4491,2002.

Hay, "SUMO-Specific Proteases: A Twist in the Tail," *Trends in Cell Biology*, 17(8): 370-376, 2007.
Kessenbrock, et al., "Matrix Metalloproteinases: Regulators of the Tumor Microenvironment," *Cell*, 141(1): 52-67, 2010.
Lopez-Otin & Matrisian, "Emerging Roles of Proteases in Tumour Suppression," *Nature*, 7: 800-808, 2007.
Thornberry, et al., "A Combinatorial Approach Defines Specificities of Members of the Caspase Family and Granzyme B," *The Journal of Biological Chemistry*, 272(29): 17907-17911,1997.
Ahmad et al., "ScFv Antibody: Principles and Clinical Application," *Clin Dev Immunol*, 2012:980250, (2012).
Ali, et al., "T Cells Expressing an Anti-B-Cell Maturation Antigen Chimeric Antigen Receptor Cause Remissions of Multiple Myeloma," *Blood*, 128:1688-1700, 2016.
Bendle et al., "Blockade of TGF-p signaling greatly enhances the efficacy of TCR gene therapy of cancer." J. Immunol, 191(6):3232-3239, (2013).
Berdeja, et al., "First-In-Human Multicenter Study of bb2121 Anti-BCMA CAR T-Cell Therapy for Relapsed/Refractory Multiple Myeloma: Updated Results.," *Journal of Clinical Oncology*, 35(15 suppl):3010-3010, 2017.
Birchenough, et al., "Equity Research: Deep Dive on Emerging Cell Therapies for Cancer," Research Report Online Wells Fargo Securities, LLC Apr. 19, 2017, retrieved on Nov. 22, 2019 from the internet https://cdn2.hubspot.net/hubfs/4625168/%5B2017%5D%20Wells%20Fargo%20-%20Deep%20on%Emerging%20CELL%20Therapies.pdf 1-94, p. 37, 5$^{th}$ paragraph.
Blat et al., "Suppression of murine colitis and its associated cancer by carcinoembryonic antigen-specific regulatory T cells," Mol Ther, 22:1018-1028, (2014).
Boissel et al., "Retargeting NK-92 cells bty means of CD19-and CD20-specific chemieric antigen receptors compares favorably with antibody-dependent cellular cytotoxicity," *Oncolmmunology*, 2(10):e26527, (2013).
Bollard et al., "Adapting a transforming growth factor p-related tumor protection strategy to enhance antitumor immunity." Blood, 99(9):3179-3187,(2002).
Brentjens et al., "CD19-targeted T cells rapidly induce molecular remissions in adults with chemotherapy-refractory acute lymphoblastic leukemia", Sci. Transl. Med., 5:177ra138, (2013).
Brudno et al., "Toxicities of chimeric antigen receptor T cells: recognition and management," Blood, 127:3321-3330, (2016).
Brunstein et al., "Umbilical cord blood-derived T regulatory cells to prevent GVHD: kinetics, toxicity profile, and clinical effect," *Blood*, 127:1044-1051, (2016).
Brusko et al., "Human antigen-specific regulatory T cells generated by T cell receptor gene transfer", PLoS One, 5:e11726, (2010).
Budde et al., "Combining a CD20 chimeric antigen receptor and an inducible caspase 9 suicide switch to improve the efficacy and safety of T cell adoptive immunotherapy for lymphoma," *PloS One*, 8(12): e82742, 2013.
Carpenter, et al. B-cell Maturation Antigen Is a Promising Target for Adoptive Tcell Therapy of Multiple Myeloma, *Clinical Cancer Research*, 19(8): 2048-2060, 2013.
Chang et al., "Rewiring T-cell responses to soluble factors with chimeric antigen receptors," Nat. Chern. Biol., 2018, 14(3):317-324.
Chen et al., "Fusion protein linkers: Property, design and functionality", Advanced Drug Delivery Reviews, vol. 65, (2003), pp. 1357-1369.
Chen, et al., "A Compound Chimeric Antigen Receptor Strategy For Targeting Multiple Myyeloma," *Leukemia*, 32(2):402-412, 2018.
Chmielewski, et al., "IL-12 Release by Engineered T Cells Expressing Chimeric Antigen Receptors Can Effectively Muster an Antigen-Independent Macrophage Response on Tumor Cells That Have Shut Down Tumor Antigen Expression," Cancer Research, 71(17): 5697-5706, 2011.
Chu, "Genetic Modification of T Cells Redirected toward CS1 Enhances Eradication of Myeloma Cells," *Clinical Cancer Research*, 20(15):3989-4000, 2014.

(56) References Cited

OTHER PUBLICATIONS

Chu, et al., "CS1-Specific Chimeric Antigen Receptor (CAR)-Engineered Natural Killer Cells Enhance In Vitro and In Vivo Antitumor Activity Against Human Multiple Myeloma," Leukemia, 28: 917-927, 2014.
Cohen, et al., "B-Cell Maturation Antigen (BCMA) Specific Chimeric Antigen Receptor T Cells (CART-BCMA) for Multiple Myeloma (MM): Initial Safety and Efficacy From a Phase I Study," Blood, 128:1147, 2016.
Corrigan-Curay et al., T-Cell Immunotherapy: Looking forward. Mol. Ther., 22, 1564-1574, 2014.
Davila et al., "Efficacy and toxicity management of 19-28z Car T cell therapy in B cell acute lymphoblastic leukemia.", Sci. Transl. Med., 6:224ra225, (2014).
Dotti et al., "Design and development of therapies using chimeric antigen receptorexpressing T-cells", Immunological Reviews, 257:107-126, (2014).
Dull et al., "A Third-Generataion Lentivirus Vector with a Conditional Packaging System," J. Virol, 72(11):8463-8471, (1998).
Ellebrecht et al., "Reengineering chimeric antigen receptor T cells for targeted therapy of autoimmune disease," Science, 353:179-184, (2016).
Extended European Search Report Issued in Corresponding European Patent Application No. 16860930.3, dated Oct. 10, 2019.
Extended European Search Report Issued in Corresponding European Patent Application No. 17845645.5, dated Mar. 24, 2020.
Foster et al., "Antitumor activity of EBC-specific T lymphocytes transduced with a dominant negative TGF-β receptor," J. Immunother., 31(5):500-505,(2008).
Gogishvili, et al., "SLAMF7-CAR T Cells Eliminate Myeloma and Confer Selective Fratricide of SLAMF7+ Normal Lymphocytes," Blood, 130: 2838-2847, 2017.
Gorelik and Flavell, "Immune-mediated eradication of tumors through the blockade of transforming growth factor-β signaling in T cells" Nat. Med., 7:1118-1122 (2001).
Hillerdal et al., "Chimeric antigen receptor-engineered T cells for the treatment of metastatic prostate cancer," BioDrugs, 29:75-89, (2015).
International Preliminary Report on Patentability Issued in Corresponding PCT Patent Application No. PCT/US2019/036731, dated Dec. 15, 2020.
International Search Report and Written Opinion Issued in Corresponding PCT Patent Application No. PCT/US2019/036731, dated Dec. 27, 2019.
International Search Report and Written Opinion issued in International Application No. PCT/US2016/059444, dated Feb. 14, 2017.
International Search Report and Written Opinion issued in International Patent Application No. PCT/IB2017/055281, dated Mar. 8, 2018.
International Search Report and Written Opinion issued in International Application No. PCT/US2015/065620, dated Mar. 28, 2016.
Kalos et al., "T cells with chimeric antigen receptors have potent antitumor effects and can establish memory in patients with advanced leukemia," Sci. Transl. Med., 3(95):95ra73, (2011).
Kelchtermans et al., "Activated CD4+CD25+ regulatory T cells inhibit osteoclastogenesis and collagen-induced arthritis", Ann. Rheum. Dis., 68:744-750, (2009).
Kelchtermans et al., "Defective CD4+CD25+ regulatory T cell functioning in collagen-induced arthritis: an important factor in pathogenesis, counter-regulated by endogenous IFN-gamma", Arthritis Res. Ther., 7:R402-415, (2005).
Kochenderfer et al., "B-cell depletion and remissions of malignancy along with cytokine-associated toxicity in a clinical trial of anti-CD19 chimeric-antigen-receptor-transduced T cells", Blood, 119:2709-2720, (2012).
Le Gall et al., "Effect of linker sequences between the antibody variable domains on the formation, stability and biological activity of a bispecific tandem diabody" Protein Engineering, Design & Selection 2004, 17(4), 357-366.

Le Gall et al., "Immunosuppressive properties of anti-CD3 single-chain Fvand diabody" Journal of Immunological Methods 2004, 285, 111-127.
Lee et al., "Current concepts in the diagnosis and management of cytokine release syndrome," Blood, 124:188-195, (2014).
Lee, et al., "An APRIL-Based Chimeric Antigen Receptor for Dual Targeting of BCMA and TACI in Multiple Myeloma," Blood, 131:746-758, 2018.
Maude, et al., "Managing Cytokine Release Syndrome Associated with Novel T Cell-Engaging Therapies," The Cancer Journal, 20(2): 119-122, 2014.
Morgan et al., "Effective treatment of collagen-induced arthritis by adoptive transfer of CD25+ regulatory T cells," Arthritis Rheum, 52:2212-2221, (2005).
Myasoedova et al., "Is the incidence of rheumatoid arthritis rising?: results from Olmsted County, Minnesota, 1955-2007", Arthritis Rheum, 62-1576-1582, (2010).
Nakamura et al., "TGF-beta 1 plays an important role in the mechanism of CD4+CD25+ regulatory T cell activity in both humans and mice," J Immunol, 164:183-190, (2004).
Office Action Issued in Corresponding Japanese Patent Application No. 2018-522004, dated Oct. 12, 2020.
Office Action Issued in Corresponding U.S. Appl. No. 15/772,403, dated Apr. 9, 2020.
Office Action Issued in Corresponding U.S. Appl. No. 15/772,403, dated Oct. 8, 2020.
Partial Search Report issued in Corresponding European Patent Application No. 16860930, dated Jun. 26, 2019.
Patel, et al., "Cancer CARtography: Charting Out a New Approach to Cancer Immunotherapy," Immunotherapy 6(6): 675-678, 2014.
Porter et al., "Chimeric antigen receptor-modified T cells in chronic lymphoid leukemia," N. Engl. J. Med., 365:725-733, (2011).
Qin et al., "Preclinical Development of Bivalent Chimeric Antigen Receptors Targeting Both CD19 and CD22", Molecular Therapy: Oncolytics, vol. 11, Dec. 21, 2018, pp. 127-137.
Qin et al., "Supplemental Information. Preclinical Development of Bivalent Chimeric Antigen Receptors Targeting Both CD19 and CD22", Molecular Therapy: Oncolytics, vol. 11.
Quatromoni et al., "T cell receptor (TCR)-transgenic CD8 lymphocytes rendered insensitive to transforming growth factor beta (TGFp) signaling mediate superior tumor regression in an animal model of adoptive cell therapy" J. Transl. Med., 10:127, (2012).
Rosenberg, "Finding suitable targets is the major obstacle to cancer gene therapy", Cancer Gene Ther., 21:45-47, (2017).
Rosenzweig, et al., "Preclinical Data Support Leveraging CS1 Chimeric Antigen Receptor T-Cell Therapy For Systemic Light Chain Amyloidosis," Cytotherapy, 19(7):861-866, 2017.
Stone et al., "A sensitivity scale for targeting T cells with chimeric antigen receptors (CARs) and bispecific T-cell engagers (BiTEs)" OncoImmunology, 1(6):863-873, (2012).
Suarez, et al., "Chimeric Antigen Receptor T Cells Secreting Anti-PD-L1 Antibodies More Effectively Regress Renal Cell Carcinoma in a Humanized Mouse Model," Oncotarget, 7(23): 34341-34355, 2016.
Supplementary European Search Report issued in European Patent Application No. 15870818, dated Apr. 10, 2018.
Szymczak-Workman et al., "Design and construction of 2A peptide-linked multicistronic vectors," Cold Spring Harb Protoc, 2012(2):199-204, (2012).
Tang et al., "Regulatory T-cell therapy in transplantation: moving to the clinic", Cold Spring Harb Perspect Med., 3:a015552, (2013).
Thornton et al., "Suppressor effector function ofCD4+CD25+ immunoregulatory T cells is antigen nonspecific", J Immunol, 164:183-190, (2000).
Wang, et al., "Lenalidomide Enhances the Function of CS1 Chimeric Antigen Receptor-Redirected T Cells Against Multiple Myeloma," Clinical Cancer Research, 24(1):106-119, 2018.
Widdifield et al., "The epidemiology of rheumatoid arthritis in Ontario, Canada." Arthritis Rheumatol, 66:786-793 (2014).
Wright et al., "Adoptive therapy with redirected primary regulatory T cells results in antigen-specific suppression of arthritis," Proc. Natl. Acad. Sci. USA, 106(45):19078-19083,(2009).

(56) References Cited

OTHER PUBLICATIONS

Wright et al., "Regulatory T-cell adoptive immunotherapy: potential for treatment of autoimmunity", *Expert Rev. Clin. Immunol.*, 7:213-225, (2011).

Wu et al., "FOXP3 controls regulatory T cell function through cooperation with NFAT", *Cell*, 126:375-387, (2006).

Yingling et al., "Development of TGF-p signalling inhibitors for cancer therapy" *Nat. Rev. Drug Discov.*, 3:1011-1022 (2004).

Zhang et al., "Adoptive Transfer of Tumor-Reactive Transforming Growth Factor--Insensitive CD8+ T Cells" *Cancer Res.* 65 (5):1761-1769. (2005).

Zhang et al., "Inhibition of TGF-p signaling in genetically engineered tumor antigenreactive T cells significantly enhances tumor treatment efficacy," Gene Ther., 20:575-580, (2012).

\* cited by examiner

CYTOTOXIC MOLECULES RESPONSIVE TO INTRACELLULAR LIGANDS FOR SELECTIVE T CELL MEDIATED KILLING

CROSS REFERENCE TO RELATED APPLICATIONS

This application is a national phase application under 35 U.S.C. § 371 of International Application No. PCT/US2015/065623, filed Dec. 14, 2015, which claims the benefit of U.S. Provisional Application No. 62/091,937, filed Dec. 15, 2014, the contents of which applications are incorporated into the present application by reference.

GOVERNMENTAL SUPPORT CLAUSE

This invention was made with government support under Grant Number OD012133 awarded by the National Institutes of Health and Grant Number 1553767 awarded by the National Science Foundation. The government has certain rights in the invention.

BACKGROUND OF THE INVENTION

"Smart drugs" or targeted therapeutics against diseased cells currently depend on the availability of membrane-bound markers or antigens present on the surface of target cells. One example of such targeted therapeutics is the use of engineered T cells that express T-cell receptors (TCRs) or chimeric antigen receptors (CARs) specific for tumor-associated antigens. However, antigens that are exclusively found on the surface of diseased cells but not on normal cells are extremely rare, and do not exist for most types of cancer.

A number of intracellular oncoproteins are known to be associated with tumor cells, including the human telomerase reverse transcriptase (hTERT). Methods of targeting cell-based therapeutics to those cytoplasmic oncoproteins are of great clinical interest. The present invention addresses this need.

Publications

Engineered versions of granzyme B (GrB) have been reported, but with the aim of targeting surface-bound antigens such as Her2 and the epidermal growth factor receptor (EGFR) (Zhao et al. 2004, Dalken et al. 2006). Specifically, GrB was fused to single-chain variable fragments (scFv) targeting Her2 or tumor growth factor α; (TGFα, a ligand for EGFR), and engineered GrB was shown to selectively kill target cells that express either Her2 or EGFR on the cell surface.

SUMO peptide fusions to proteins have been reported as a tool for protein purification (Malakov et al. 2004). The ability to regulate protein function via protein conformational changes imposed by the binding activity of fusion partners attached to the protein has been demonstrated in a proof-of-concept study (Dueber et al. 2003).

SUMMARY OF THE INVENTION

Compositions and methods are provided for the cell-mediated targeted killing of diseased cells based on the presence of an intracellular antigen, rather than a surface-bound marker. This invention is optionally combined with tumor-targeting TCRs and CARs to enable a two-step verification process before killing a target cell, thereby increasing the specificity and safety profile of T-cell therapy for a variety of diseases, including cancer. The targeting cells are modified to express a cytotoxic protein that is delivered into a targeted cell, and after delivery is selectively activated by the presence of a cytoplasmic protein of interest.

In one embodiment of the invention, the cytotoxic molecule is a Granzyme B (GrB) polypeptide, which is a serine protease most commonly found in the granules of cytotoxic lymphocytes (CTLs), natural killer cells (NK cells) and cytotoxic T cells. It is secreted by these cells along with the pore forming protein perforin to mediate apoptosis in target cells. In the compositions of the invention, GrB is modified to render its cytotoxic enzymatic functions inactive, until the presence of an intracellular antigen unlocks the GrB molecule to enable enzymatic activities.

In one embodiment of the invention, binding partners designated herein as an "interrogation domain" (ID) and a "truncated oncoprotein" (TO) are fused internal to and/or at the termini of the GrB polypeptide. In embodiments where the ID is inserted within the GrB protein, the point of insertion may be within an exposed loop. Insertion sites include, without limitation, between the E188 and I189 residues of GrB. In such embodiments the TO may be fused to the C-terminus of the protein. Optionally a linker is used to join one or both of the ID and the TO to GrB.

The ID may be an scFv, nanobody, or other specific binding partner to an oncoprotein of interest. The truncated oncoprotein is an inactive form of an oncoprotein of interest in the targeted cell or other specific binding partner to the ID. The ID is selected such that the affinity of the ID for the TO is lower than the affinity for the native oncoprotein, e.g. at least about 5-fold lower, at least about 10-fold lower, at least about 20 fold lower, at least about 100-fold lower, or more.

The GrB thus modified can be secreted from a T cell (or other cell), but is inactive, i.e. in a closed conformation, due to the binding of the ID to the TO. Upon contact with a native form of the oncoprotein or specific binding partner for which the ID has a higher affinity than for the TO version, the TO is displaced and GrB is unlocked and able to mediate its cytotoxic effects on the targeted cell.

In some embodiments, the specific binding partner of interest is human telomerase reverse transcriptase (hTERT). In such embodiments, the ID specifically binds to an epitope of hTERT. For example, the ID may be an scFv that specifically binds to an epitope of hTERT. In some such embodiments, the TO comprises a truncated and non-oncogenic form of hTERT, e.g. hTERT lacking the catalytic domain. The TO may comprise or consist of the hTERT long N-terminal extension (NTE) and/or short C-terminal extension (CTE) in the absence of the catalytic domain.

Figure 6:
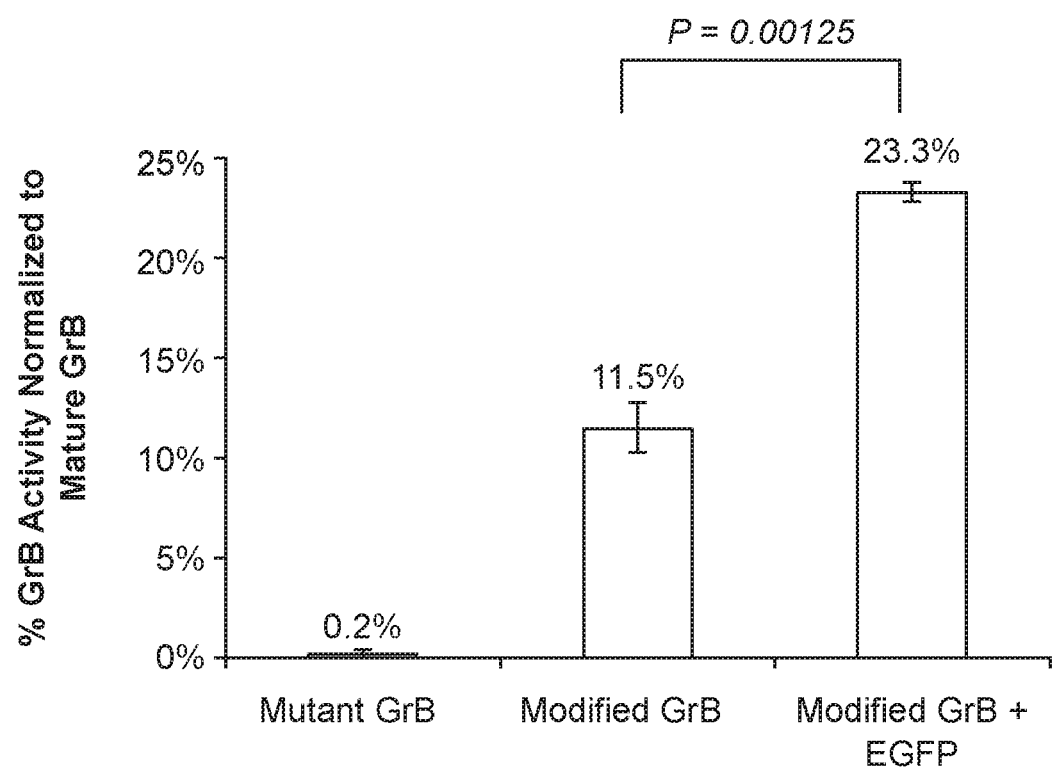

In an alternative embodiment, a fusion protein is linked to the N-terminus of the mature form of GrB via a cleavage peptide that is recognized by a cancer-associated protease, where the protease cleaves to generate a flush cut, i.e. removal of the fusion protein and the entire cleavage peptide from the GrB. For example, without limitation, the first 97 amino acids of the human small ubiquitin-related modifier 1 (SUMO1) peptide can be fused to the N-terminus of the mature form of GrB, which excludes the signal peptide and the GE dipeptide that comprise the first 20 amino acids of the GrB zymogen. The SUMO1 fusion renders GrB enzymatically inactive. Sentrin-specific protease 1 (SENP1), which is expressed in certain cancer cells, can cleave the SUMO1 peptide and activate GrB's cytotoxic activity, e.g. in the treatment of prostate cancer. An exemplary construct is shown in FIG. 6.

For each of the embodiments described above, modifications may be made to enhance expression and purification. For example, a secretion signal peptide and a 6×-histidine tag may be attached to the N-terminus of the engineered GrB. This engineered GrB molecule can be expressed and secreted by producer cell lines such as human embryonic kidney (HEK) 293T cells, purified using a nickel column, and concentrated by size-exclusion membrane filtration. The concentrated protein can be applied to target cells for selective killing of cells expressing the target antigen.

In other embodiments, the GrB signal peptide is attached to the N-terminus of the engineered GrB. This engineered GrB molecule can be expressed by effector cells such as T cells, and the effector cells can be used to specifically lyse target-antigen-expressing cells that are recognized by the T cells.

In yet another embodiments, a secretion peptide is attached to the N-terminus of the engineered GrB. This engineered GrB molecule can be expressed by a mammalian effector cell line, and the effector cells can be used to specifically lyse SENP1-expressing target cells co-cultured with the effector cells.

Nucleic acids encoding the modified proteins of the invention are generated, and may be provided in a suitable vector system, e.g. viral delivery system, plasmid, and the like. The nucleic acids are used to genetically modify a host cell of interest, e.g. autologous T cells, cell lines, etc. The cells thus modified are used in a method of targeted killing of cells, e.g. cancer cells.

In some embodiments, a method of killing a cancer cell in an individual is provided, comprising the step of providing to the individual a therapeutically effective amount of a therapeutic cell of the invention, including an effector cell, such as a T cell, NK cell, NKT cell of the invention, for example. The targeting cell may have affinity for the tumor cell as a result of innate immunity, as a result of expression of an immune receptor, as a result of engineering to comprise a CAR, and the like. Any method of the invention may further comprise the step of delivering to the individual an additional cancer therapy, such as surgery, radiation, hormone therapy, chemotherapy, immunotherapy, or a combination thereof, for example.

In embodiments of the invention, a kit is provided comprising cells comprising a modified GrB protein of the invention.

BRIEF DESCRIPTION OF THE DRAWINGS

For a more complete understanding of the present invention, reference is now made to the following descriptions taken in conjunction with the accompanying drawing.

FIG. 1. Schematic of engineered granzyme B (GrB) with interrogation domain (ID) and truncated oncoprotein (TO) attached to the N- and C-termini of the GrB, respectively. In the absence of oncoprotein, ID and TO bind to each other to form a strained protein conformation that inactivates GrB. Free oncoprotein, which has high affinity for ID, binds to ID by competitively displacing TO, thereby opening the protein conformation and activating GrB.

FIG. 2. Schematic of engineered granzyme B (GrB) with interrogation domain (ID) and truncated oncoprotein (TO) attached to an internal loop and the C-terminus of the GrB, respectively. In the absence of oncoprotein, ID and TO bind to each other to form a strained protein conformation that inactivates GrB. Free oncoprotein, which has high affinity for ID, binds to ID by competitively displacing TO, thereby opening the protein conformation and activating GrB.

FIG. 3. Schematic of engineered granzyme B (GrB) with inhibitory "pro-domain" fused to the N-terminus of GrB. In the absence of cancer-associated protease, the inhibitory domain remains attached to GrB and blocks GrB activity by preventing proper folding of the protein's N-terminus, Presence of the cognate protease precisely removes the inhibitory domain to expose the N-terminus of mature GrB, thereby activating enzymatic activity.

FIG. 4. Schematic illustrating the strategy for using engineered GrB to specifically trigger apoptosis in diseased cells that express a cognate oncoprotein. Engineered GrB are delivered by T cells to target cells upon recognition of surface-bound antigens by T-cell receptors or chimeric antigen receptors. (A) Absence of oncoprotein keeps GrB switch inactive and prevents target-cell killing. (B) Presence of oncoprotein switches GrB activity to trigger target cell apoptosis.

FIG. 5. Enzymatic activity of GrB with or without fusion partners. HEK 293T cells were transiently transfected with various GrB constructs, and cell lysates were reacted with Ac-IEPD-pNA, which generates a chromogenic product detectable at 405 nm upon cleavage by GrB. GrB was either expressed in the mature form by itself, fused in the N-terminus to an anti-GFP nanobody, or fused in the C-terminus to the I146N mutant of ECFP. Fusion proteins either contained no linker between the two fusion partners, or contained a glycine-serine peptide linker. N-linker: GSSGSGSSGSGSSG. C-linker: GGGGS. Reported values are the means of triplicates with error bars indicating ±1 standard deviation.

FIG. 6. Ligand-responsive enzymatic activity of GrB with internally inserted ID.

Plasmids encoding a His-tagged, modified GrB containing an anti-GFP nanobody inserted between E188 and I189 as well as ECFP fused its C-terminus were transiently transfected into HEK 293T cells. Mature GrB and an inactive S183A mutant GrB were included as positive and negative controls, respectively. Proteins were purified from HEK lysates via $Ni^{2+}$ affinity chromatography followed by enterokinase treatment to remove the His tag. Purified proteins were co-incubated with buffer only or 2 μM EGFP, and subsequently assayed for the ability to cleave Ac-IEPD-pNA substrates. Enzymatic activity was quantified by measuring absorbance at 405 nm. Reported values are the means of triplicates and normalized to that of mature GrB. P-value was calculated by two-tailed Student's t test. Error bars indicate ±1 standard deviation.

FIG. 7. SENP1 activates SUMO-GrB. (A) Western blot of $Ni^{2+}$ affinity chromatography-purified SUMO-GrB or GrB co-incubated with Mock-transfected or SENP1-overexpressing HEK lysate. (B) GrB activity for purified mature GrB S183A, SUMO-GrB, or mature GrB following co-incubation with buffer only, HEK Mock lysate, or HEK SENP1-overexpressing lysate. GrB activity was quantified and normalized as described in FIG. 6. Reported values are the means of triplicates with error bars indicating ±1 standard deviation.

FIG. 8. SUMO-GrB activity is regulated by SENP1 in a dose-dependent manner. SENP1 protein level in the lysate of various cell lines was quantified by western blots. Purified SUMO-GrB was co-incubated with the lysates of each cell line and subsequently reacted with Ac-IEPD-pNA. GrB cleavage activity was quantified by measuring absorbance at 405 nm and the rate of absorbance increase was plotted against SENP1 expression levels quantified by western blot. Reported values are the means of triplicates with error bars indicating ±1 standard deviation.

FIG. 9. Plasmid map for engineered GrB with ID and TO fused to N- and C-termini.

FIG. 10. Plasmid map for engineered GrB with internal ID insertion and C-terminal TO fusion.

FIG. 11. Plasmid map for SUMO-modified GrB.

DETAILED DESCRIPTION OF THE EMBODIMENTS

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein embodiments which are disclosed and still obtain a like or similar result without departing from the spirit and scope of the invention.

The term "genetic modification" means any process that adds, deletes, alters, or disrupts an endogenous nucleotide sequence and includes, but is not limited to viral mediated gene transfer, liposome mediated transfer, transformation, transfection and transduction, e.g., viral mediated gene transfer such as the use of vectors based on DNA viruses such as lentivirus, adenovirus, retroviruses, adeno-associated virus and herpes virus.

"Variant" refers to polypeptides having amino acid sequences that differ to some extent from a native sequence polypeptide. Ordinarily, amino acid sequence variants will possess at least about 80% sequence identity, more preferably, at least about 90% homologous by sequence. The amino acid sequence variants may possess substitutions, deletions, and/or insertions at certain positions within the reference amino acid sequence.

To "treat" a disease or a disorder, such as cancer, means to take either therapeutic measures or preventative measures to lessen or abate the disease or disorder. Such treatment includes prevention, alleviation of symptoms, diminishment or stabilization of scope, and/or remission.

"Cancer" refers to cells undergoing uncontrolled cellular growth. Examples of cancer include colorectal cancer and head and neck cancer. A "chemotherapeutic agent" is a chemical compound useful in the treatment of cancer.

Cancers of interest for treatment include carcinomas, e.g. breast, colon, colorectal, prostate, pancreatic, melanoma, ductal, endometrial, stomach, dysplastic oral mucosa, invasive oral cancer, non-small cell lung carcinoma, thyroid, transitional and squamous cell urinary carcinoma, etc.; neurological malignancies, e.g. neuroblastoma, gliomas, etc.; hematological malignancies, e.g. childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like. In some embodiments the cancer is prostate cancer.

The term "therapeutically effective amount" refers to an amount of a compound or molecule effective to treat a disease or disorder.

The term "specific binding member" as used herein refers to a member of a specific binding pair, i.e. two molecules, usually two different molecules, where one of the molecules through chemical or physical means specifically binds to the other molecule. The complementary members of a specific binding pair are sometimes referred to as a ligand and receptor; or receptor and counter-receptor. Specific binding indicates that the agent can distinguish a target antigen, or epitope within it, from other non-target antigens. It is specific in the sense that it can be used to detect a target antigen above background noise ("non-specific binding"). For example, a specific binding partner can detect a specific sequence or a topological conformation. A specific sequence can be a defined order of amino acids or a defined chemical moiety (e.g., where an antibody recognizes a phosphotyrosine or a particular carbohydrate configuration, etc.) which occurs in the target antigen. The term "antigen" is issued broadly, to indicate any agent which elicits an immune response in the body. An antigen can have one or more epitopes.

Binding pairs of interest include antigen and antibody specific binding pairs, complementary nucleic acids, peptide-MHC-antigen complexes and T cell receptor pairs, biotin and avidin or streptavidin; carbohydrates and lectins; complementary nucleotide sequences; peptide ligands and receptor; effector and receptor molecules; hormones and hormone binding protein; enzyme cofactors and enzymes; enzyme inhibitors and enzymes; and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies; and T cell antigen receptors, and their cognate MHC-peptide conjugates. Suitable antigens may be haptens, proteins, peptides, carbohydrates, etc. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

The affinity of a specific binding pair refers to affinity measurements as known in the art, and may be empirically tested, e.g. by biacore, etc. Generally specific binding refers to binding with a Kd of at least about $10^{-7}$, and may be $10^{-9}$, $10^{-9}$, $10^{-19}$, $10^{-11}$, etc. As discussed above, where the construct comprises a TO, the binding affinity of the ID for the TO is less than the affinity for the native oncoprotein, e.g. at least about 5-fold lower, at least about 10-fold lower, at least about 20-fold lower, at least about 100-fold lower, or more.

Granzyme B is encoded by GZMB on chromosome 14q.11.2 which is 3.2 kb long consisting of 4 introns and 5 exons. It is one of the most abundant granzymes. The enzyme is initially in an inactive precursor zymogen form, with an additional amino terminal peptide sequence. Granzyme B's structure consists of two 6 stranded β sheets with 3 trans domain segments. Granzyme B contains the catalytic triad histidine-aspartic acid-serine in its active site and preferentially cleaves after an aspartic acid residue situated in the P1 position. Granzyme B is active at a neutral pH and is therefore inactive in the acidic CTL granules. The enzyme is also rendered inactive when bound by serglycin in the granules to avoid apoptosis triggering inside the cytotoxic T cells themselves.

Granzyme B may be released with perforin which inserts into a target cell's plasma membrane forming a pore of a size appropriate for granzyme B to pass into the targeted cell.

Alternatively, once released, granzyme B can bind to negatively charged heparan sulphate containing receptors on a target cell and become endocytosed. The vesicles that carry the enzyme inside then burst, exposing granzyme b to the cytoplasm and its substrates.

Once activated by the target granzyme B can cleave and activate initiator caspases 8 and 10, and executioner caspases 3 and 7 which trigger apoptosis. Granzyme B can also cleave BID leading to BAX/BAK oligomerisation and cytochrome c release from the mitochondria. Granzyme B can cleave ICAD leading to DNA fragmentation and the laddering pattern associated with apoptosis.

Telomerase. A hallmark of human cancer cells is the up-regulation of telomere maintenance mechanisms that prevent telomere shortening and confer unlimited replicative capacity. In normal cells the inability of conventional DNA polymerases to fully replicate the ends of linear chromosomes results in telomere erosion during cell division. Telomerase is a ribonucleoprotein (RNP) reverse transcriptase (RT) complex that minimally contains a catalytic protein subunit, the telomerase reverse transcriptase (TERT), and an RNA subunit, the telomerase RNA (TR). TERT uses a small RNA template within TR to reverse transcribe telomeric nucleotides onto the ss 3'-ends of chromosomes in vivo. TERT proteins are structurally defined by conserved RT and telomerase-specific domains. The structural organization of TERT can be divided into at least three modular regions: 1) a long N-terminal extension (NTE) that contains conserved domains and an unstructured linker region, 2) a central catalytic RT domain with seven evolutionarily-conserved RT motifs, and 3) a short C-terminal extension (CTE). TERT-specific domains in the NTE and CTE contribute to the biochemical properties that distinguish telomerase from prototypical RT's. (see Wyatt et al. (2009) PLoS ONE 4(9): e7176).

SUMO. There are 3 confirmed SUMO isoforms in humans; SUMO-1, SUMO-2, and SUMO-3. SUMO-2/3 show a high degree of similarity to each other and are distinct from SUMO-1. SUMO-4 shows similarity to -2/3 but it is as yet unclear whether it is a pseudogene or merely restricted in its expression pattern. Sumoylation is a post-translational modification involved in various cellular processes, such as nuclear-cytosolic transport, transcriptional regulation, apoptosis, protein stability, response to stress, and progression through the cell cycle. The process of sumoylation involves the use of endogenous Small Ubiquitin-like Modifier (or SUMO) proteins, which are covalently attached to and detached from other proteins in cells to modify the function of those targeted proteins. SUMO proteins are similar to ubiquitin, and sumoylation is directed by an enzymatic cascade analogous to that involved in ubiquitination. In contrast to ubiquitin, SUMO is not used to tag proteins for degradation. Mature SUMO is produced when the last four amino acids of the C-terminus have been cleaved off to allow formation of an isopeptide bond between the C-terminal glycine residue of SUMO and an acceptor lysine on the target protein.

The term "gene" means the segment of DNA involved in producing a polypeptide chain; it includes regions preceding and following the coding region "leader and trailer" as well as intervening sequences (introns) between individual coding segments (exons). Some genes may be developed which lack, in whole or in part, introns. Some leader sequences may enhance translation of the nucleic acid into polypeptides.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, a "vector" may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. Transcription of the DNA encoding the polypeptides of the present invention by higher eukaryotes is increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

Oncoproteins, as used herein, refers to the genes and gene products that are characteristic of cancer cells. In preferred embodiments, the oncoprotein is substantially absent from non-transformed cells, e.g. a novel fusion protein, hTERT, etc. A representative list of oncoproteins is provided in Table 1.

| Oncogene | Function/Activation | Cancer* |
|---|---|---|
| abl | Promotes cell growth through tyrosine kinase activity | Chronic myelogenous leukemia |
| Af4/hrx | Fusion affects the hrx transcription factor/methyltransferase. hrx is also called MLL, ALL1 and HTRX1 | Acute leukemias |
| akt-2 | Encodes a protein-serine/threonine kinase | Ovarian cancer |
| alk | Encodes a receptor tyrosine kinase | Lymphomas |
| alk/npm | Translocation creates fusion protein with nucleophosmin(npm) | Large cell lymphomas |
| aml1 | Encodes a transcription factor | Acute myeloid leukemia |
| aml1/mtg8 | New fusion protein created by translocation | Acute leukemias |
| axl | Encodes a receptor tyrosine kinase | Hematopoietic cancers |
| bcl-2, 3, 6 | Block apoptosis (programmed cell death) | B-cell lymphomas and leukemias |

-continued

| Oncogene | Function/Activation | Cancer* |
|---|---|---|
| bcr/abl | New protein created by fusion of bcr and abl triggers unregulated cell growth | Chronic myelogenous and acute lymphotic leukemia |
| c-myc | Transcription factor that promotes cell proliferation and DNA synthesis | Leukemia; breast, stomach, lung, cervical, and colon carcinomas; neuroblastomas and glioblastomas |
| dbl | Guanine nucleotide exchange factor | Diffuse B-cell lymphoma |
| dek/can | New protein created by fusion | Acute myeloid leukemia |
| E2A/pbx1 | New protein created by fusion | Acute pre B-cell leukemia |
| egfr | Cell surface receptor that triggers cell growth through tyrosine kinase activity | Squamous cell carcinoma |
| enl/hrx | Fusion protein created by a translocation t(11; 19). | Acute leukemias |
| erg/TLS | Fusion protein created by t(16:21) translocation. The erg protein is a transcription factor. | Myeloid leukemia |
| erbB | Cell surface receptor that triggers cell growth through tyrosine kinase activity | Glioblastomas, and squamous cell carcinomas |
| erbB-2 | Cell surface receptor that triggers cell growth through tyrosine kinase activity; also known as HER2 or neu | Breast, salivary gland, and ovarian carcinomas |
| ets-1 | Transcription factor | Lymphoma |
| ews/fli-1 | Fusion protein created by t(11:22) translocation. | Ewing Sarcoma |
| fms | Tyrosine kinase | Sarcoma |
| fos | Transcription factor for API | Osteosarcoma |
| fps | Tyrosine kinase | Sarcoma |
| gli | Transcription factor | Glioblastoma |
| gsp | Membrane associated G protein | Thyroid carcinoma |
| HER2/neu | overexpression of signaling kinase due to gene amplification | Breast and cervical carcinomas |
| hox11 | Transcription factor | Acute T-cell leukemia |
| hst | Encodes fibroblast growth factor | Breast and squamous cell carcinomas |
| int-2 | Encodes a fibroblast growth factor | Breast and squamous cell carcinomas |
| jun | Transcription factor for API | Sarcoma |
| kit | Tyrosine kinase | Sarcoma |
| KS3 | Herpes virus encoded growth factor | Kaposi's sarcoma |
| K-sam | Fibroblast growth factor receptor | Stomach carcinomas |
| Lbc | Guanine nucleotide exchange factor | Myeloid leukemias |
| lck | Tyrosine kinase | T-cell lymphoma |
| lmo1, lmo2 | Transcription factors | T-cell lymphoma |
| L-myc | Transcription factor | Lung carcinomas |
| lyl-1 | Transcription factor | Acute T-cell leukemia |
| lyt-10 | Transcription factor. Also called NFκB2 | B-cell lymphoma |
| lyt-10/C alpha1 | Fusion protein formed by the (10; 14)(q24; q32) translocation of lyt-10 next to the C alpha 1 immunoglobulin locus. | |
| mas | Angiotensin receptor | Mammary carcinoma |
| mdm-2 | Encodes a protein that inhibits and leads to the degradation of p53 | Sarcomas |
| mll | Transcription factor/methyltransferase (also called hrx and ALL1) | Acute myeloid leukemia |
| mos | Serine/threonine kinase | Lung cancer |
| mtg8/aml1 | Fusion of transcription represser to factor to a transcription factor. AML1 is also known as RUNX1. | Acute leukemias |
| myb | Transcription factor | Colon carcinoma and leukemias |
| MYH11/CBFB | New protein created by fusion of transcription factors via an inversion in chromosome 16. | Acute myeloid leukemia |
| neu | Tyrosine kinase. Also called erbB-2 or HER2 | Glioblastomas, and squamous cell carcinomas |
| N-myc | Cell proliferation and DNA synthesis | Neuroblastomas, retmoblastomas, and lung carcinomas |
| ost | Guanine nucleotide exchange factor | Osteosarcomas |
| pax-5 | Transcription factor | Lympho-plasmacytoid B-cell lymphoma |
| pbx1/E2A | Fusion protein formed via t(1:19) translocation. Transcription factor | Acute pre B-cell leukemia |
| pim-1 | Serine/threonine kinase | T-cell lymphoma |
| PRAD-1 | Encodes cyclin D1. Involved in cell cycle regulation. | Breast and squamous cell carcinomas |
| raf | Serine/threonine kinase | Many cancer types |
| RAR/PML | Fusion protein caused by t(15:17) translocation. Retinoic acid receptor. | Acute premyelocytic leukemia |
| rasH | G-protein. Signal transduction. | Bladder carcinoma |
| rasK | G-protein. Signal transduction | Lung, ovarian, and bladder carcinoma |

| Oncogene | Function/Activation | Cancer* |
|---|---|---|
| rasN | G-protein. Signal transduction | Breast carcinoma |
| rel/nrg | Fusion protein formed by deletion in chromosome 2. Transcription factor. | B-cell lymphoma |
| ret | Cell surface receptor. Tyrosine kinase | Thyroid carcinomas, multiple endocrine neoplasia type 2 |
| rhom1, rhom2 | Transcription factors | Acute T-cell leukemia |
| ros | Tyrosine kinase | Sarcoma |
| ski | Transcription factor | Carcinomas |
| sis | Growth factor | Glioma, fibrosarcoma |
| set/can | Fusion protein formed by rearrangement of chromosome 9. Protein localization | Acute myeloid leukemia |
| src | Tyrosine kinase | Sarcomas |
| tal1, tal2 | Transcription factor. TAL1 is also called SCL | Acute T-cell leukemia |
| tan-1 | Altered form of Notch (a cellular receptor) formed by t(7:9) translocation | Acute T-cell leukemia |
| Tiam1 | Guanine nucleotide exchange factor | T-lymphoma |
| TSC2 | GTPase activator | Renal and brain tumors |
| trk | Receptor tyrosine kinase | Colon and thyroid carcinomas |

The term "antibody" includes monoclonal antibodies, polyclonal antibodies, dimers, multimers, multispecific antibodies and antibody fragments that may be human, mouse, humanized, chimeric, or derived from another species. A "monoclonal antibody" is an antibody obtained from a population of substantially homogeneous antibodies that is being directed against a specific antigenic site.

"Antibody or functional fragment thereof" means an immunoglobulin molecule that specifically binds to, or is immunologically reactive with a particular antigen or epitope, and includes both polyclonal and monoclonal antibodies. The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, and tetrabodies). The term functional antibody fragment includes antigen binding fragments of antibodies, including e.g., Fab', F(ab')$_2$, Fab, Fv, rIgG, and scFv fragments. The term scFv refers to a single chain Fv antibody in which the variable domains of the heavy chain and of the light chain of a traditional two chain antibody have been joined to form one chain.

As used herein, the term "tumor microenvironment" refers to any and all elements of the tumor milieu that creates a structural and or functional environment for the malignant process to survive and/or expand and/or spread.

Highly selective targeted cell therapies, for example T cell therapies, are emerging as effective non-toxic modalities for the treatment of cancer. Malignancies are complex diseases where multiple elements contribute to the overall pathogenesis through both distinct and redundant mechanisms. Hence, targeting different cancer-specific markers simultaneously could result in better therapeutic efficacy.

Embodiments of the invention utilize a modified GrB protein as an artificial molecule that enables immune cells (T cells) to specifically and distinctly recognize and attack cancer cells based on the presence of a cytoplasmic target. The modification is optionally performed in combination with a CAR targeting construct, where the CAR is an artificial molecule that can be grafted onto T cells using genetic engineering technology to render them specific to a target of interest.

Embodiments of the invention include cells that express a modified GrB protein of the invention. The cell may be of any kind, including an immune cell capable of expressing the modified GrB protein of the invention for cancer therapy or a cell, such as a bacterial cell, that harbors an expression vector that encodes the modified GrB protein of the invention. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a cytotoxic T cell (also known as TC, Cytotoxic T Lymphocyte, CTL, T-Killer cell, cytolytic T cell, CD8+ T-cells or killer T cell); NK cells and NKT cells are also encompassed in the invention.

The cells can be autologous cells, syngeneic cells, allogenic cells and even in some cases, xenogeneic cells. In many situations one may wish to be able to kill the modified CTLs, where one wishes to terminate the treatment, the cells become neoplastic, in research where the absence of the cells after their presence is of interest, or other event. For this purpose one can provide for the expression of certain gene products in which one can kill the modified cells under controlled conditions, such as inducible suicide genes.

By way of illustration, cancer patients or patients susceptible to cancer or suspected of having cancer may be treated as follows. Cells modified as described herein may be administered to the patient and retained for extended periods of time. The individual may receive one or more administrations of the cells. In some embodiments, the genetically modified cells are encapsulated to inhibit immune recognition and placed at the site of the tumor. The cells may be injected at the tumor site or injected intravenously, for example.

In particular cases the individual is provided with therapeutic immune cells, e.g. T cells comprising one or both of CD4+ T cells, CD8+ T cells; which immune cells are modified to comprise a modified GrB protein of the invention. Typically the immune cells are engineered to knock out the endogenous GrB gene. Genetic knockout can be accomplished by any convenient method as known in the art, e.g. editing with CRISPR/Cas9; introduction of sequences encoding a GrB specific siRNA, shRNA, and the like. The cells may be delivered at the same time or at different times as another type of cancer therapy. The cells may be delivered in the same or separate formulations as another type of cancer therapy. The cells may be provided to the individual in separate delivery routes as another type of cancer therapy. The cells may be delivered by injection at a tumor site or intravenously or orally, for example. Routine delivery routes for such compositions are known in the art.

Expression vectors that encode the modified GrB protein of the invention can be introduced as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example, one can knock out an endogenous gene and replace it (at the same locus or elsewhere) with the gene encoded for by the construct using materials and methods as are known in the art for homologous recombination; or with materials and methods known in the art for genetic editing. For homologous recombination, one may use either omega or O-vectors. Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

The cells that have been modified with the construct(s) are then grown in culture under selective conditions and cells that are selected as having the construct may then be expanded and further analyzed, using, for example; the polymerase chain reaction for determining the presence of the construct in the host cells. Once the modified host cells have been identified, they may then be used as planned, e.g. expanded in culture or introduced into a host organism.

Depending upon the nature of the cells, the cells may be introduced into a host organism, e.g. a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically acceptable medium.

The cells may be administered as desired. Depending upon the response desired, the manner of administration, the life of the cells, the number of cells present, various protocols may be employed. The number of administrations will depend upon the factors described above at least in part.

In some embodiments AAV, retroviral or lentiviral vectors are used to deliver the modified GrB protein of the invention to a T cell.

Adeno associated virus (AAV) is an attractive vector system for use in the cells of the present invention as it has a high frequency of integration and it can infect nondividing cells, thus making it useful for delivery of genes into mammalian cells, for example, in tissue culture or in vivo. AAV has a broad host range for infectivity. Details concerning the generation and use of rAAV vectors are described in U.S. Pat. Nos. 5,139,941 and 4,797,368, each incorporated herein by reference.

Retroviruses are useful as delivery vectors because of their ability to integrate their genes into the host genome, transferring a large amount of foreign genetic material, infecting a broad spectrum of species and cell types and of being packaged in special cell lines.

Lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2 and the Simian Immunodeficiency Virus: SIV. Recombinant lentiviral vectors are capable of infecting non-dividing cells and can be used for both in vivo and ex vivo gene transfer and expression of nucleic acid sequences.

Any of the compositions described herein may be comprised in a kit. In a non-limiting example, one or more cells for use in cell therapy and/or the reagents to generate one or more cells for use in cell therapy that harbors recombinant expression vectors may be comprised in a kit. The kit components are provided in suitable container means. Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, if osfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing and also combinations thereof.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

All references cited in this specification are hereby incorporated by reference in their entirety. The following examples are solely for the purpose of illustrating one embodiment of the invention.

EXPERIMENTAL

Figure 2:
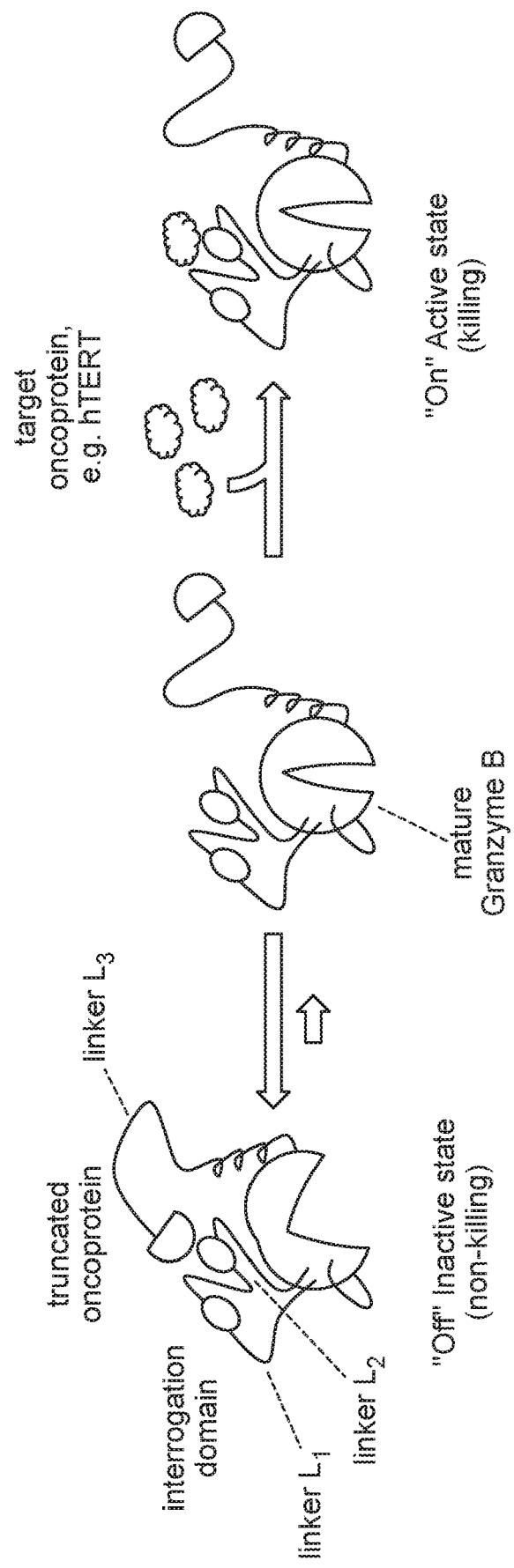
Figure 3:
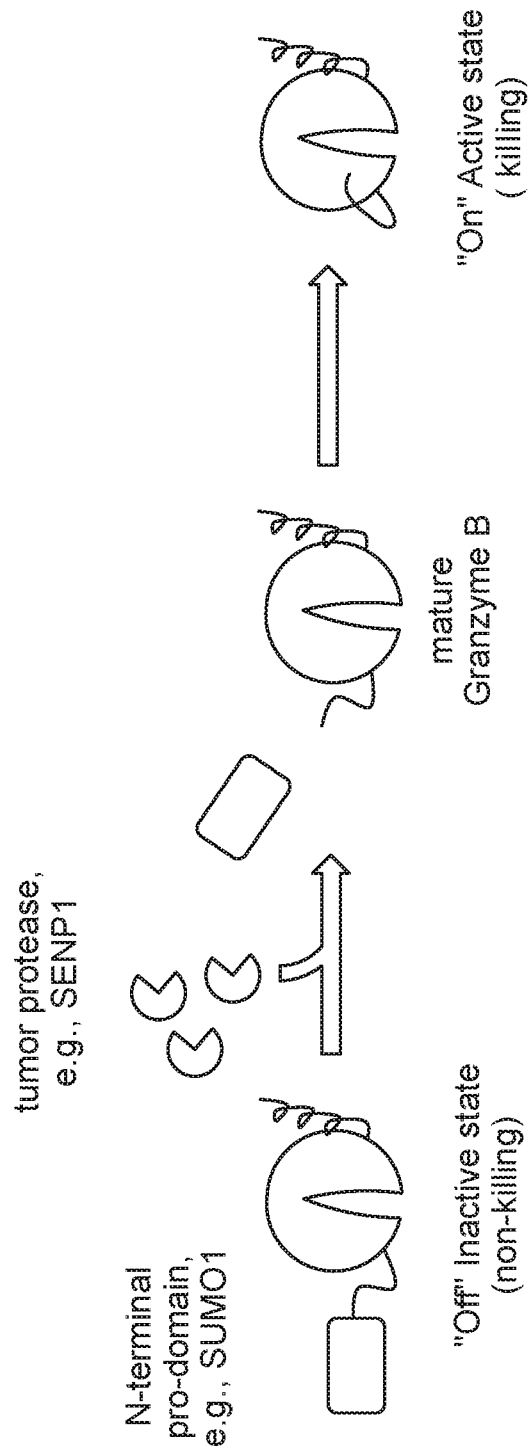
Figure 4:
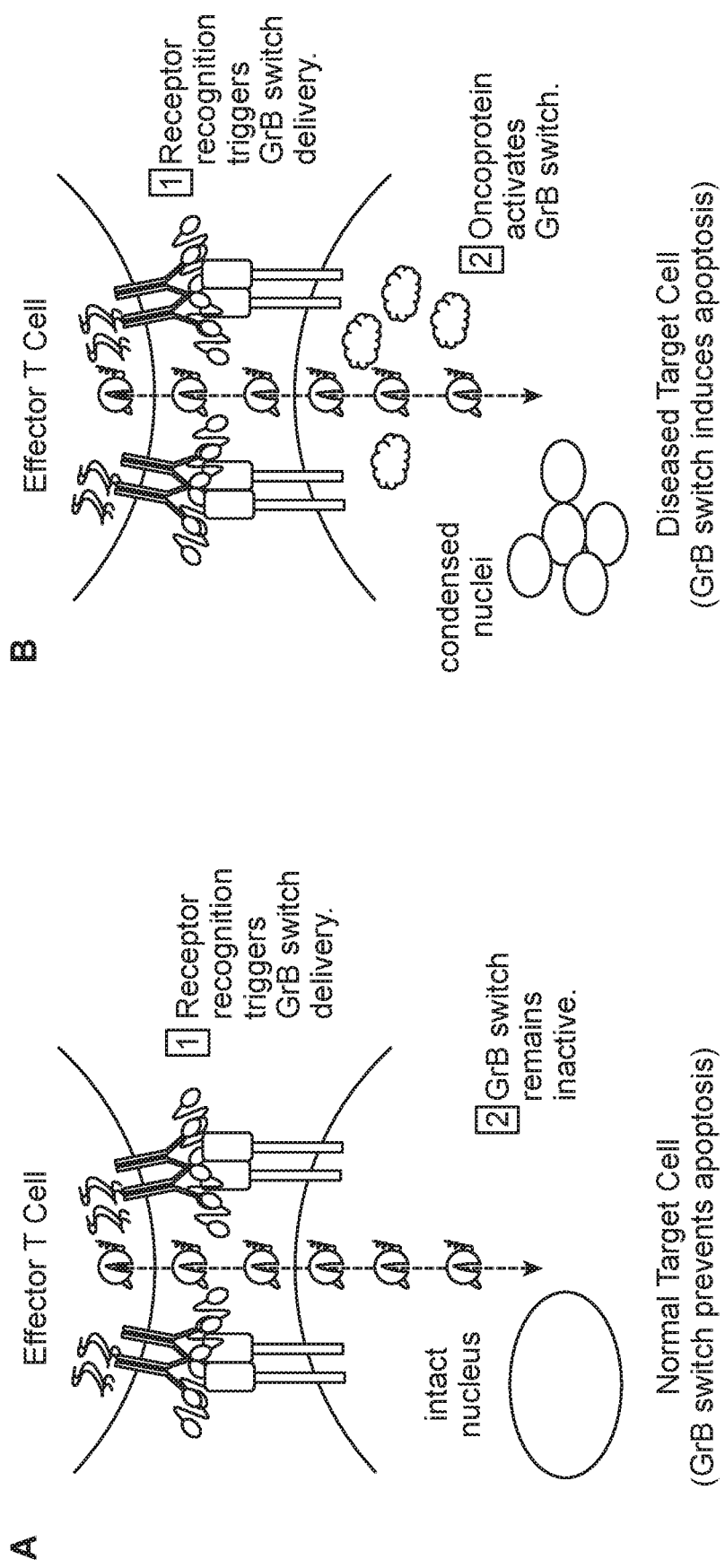
Figure 5:
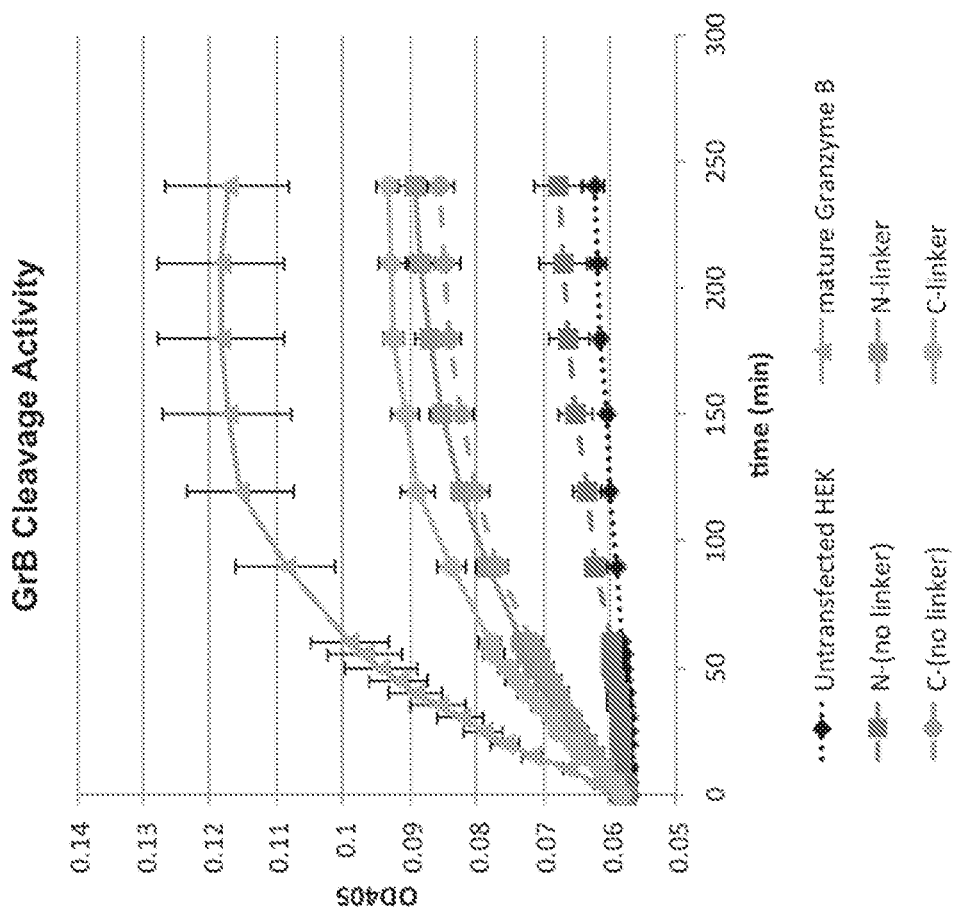
Figure 9:
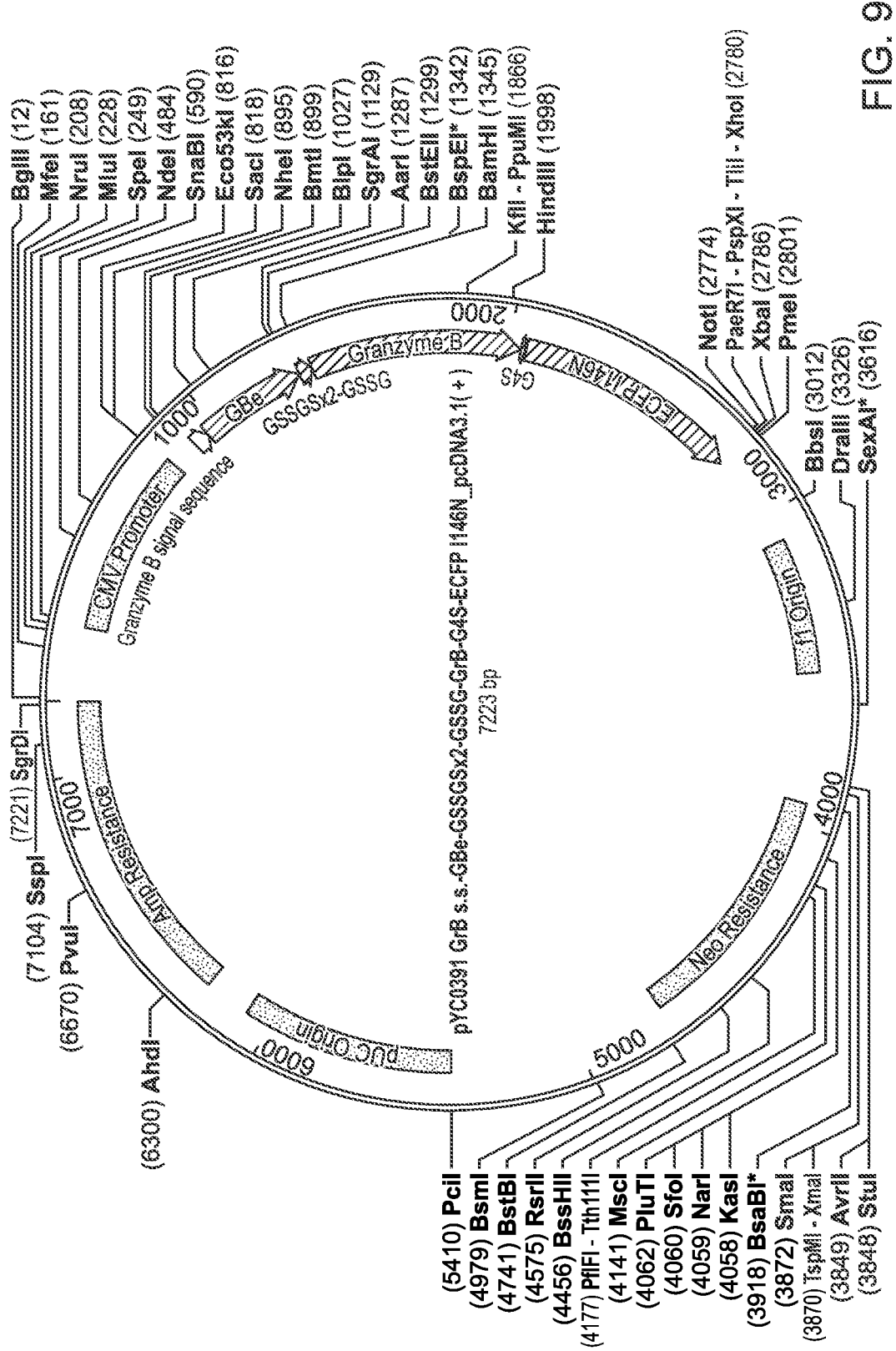
Figure 10:
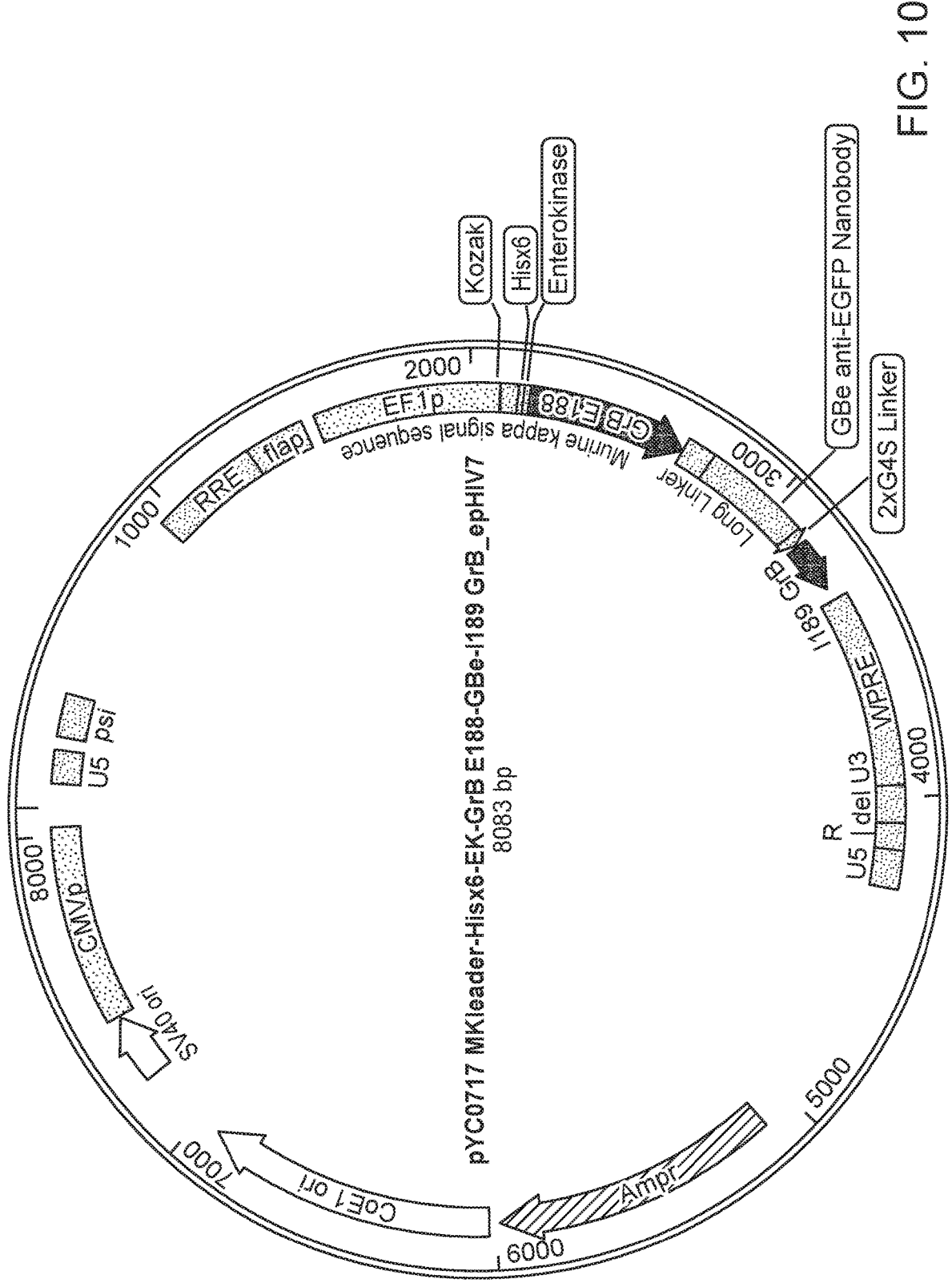
Figure 11:
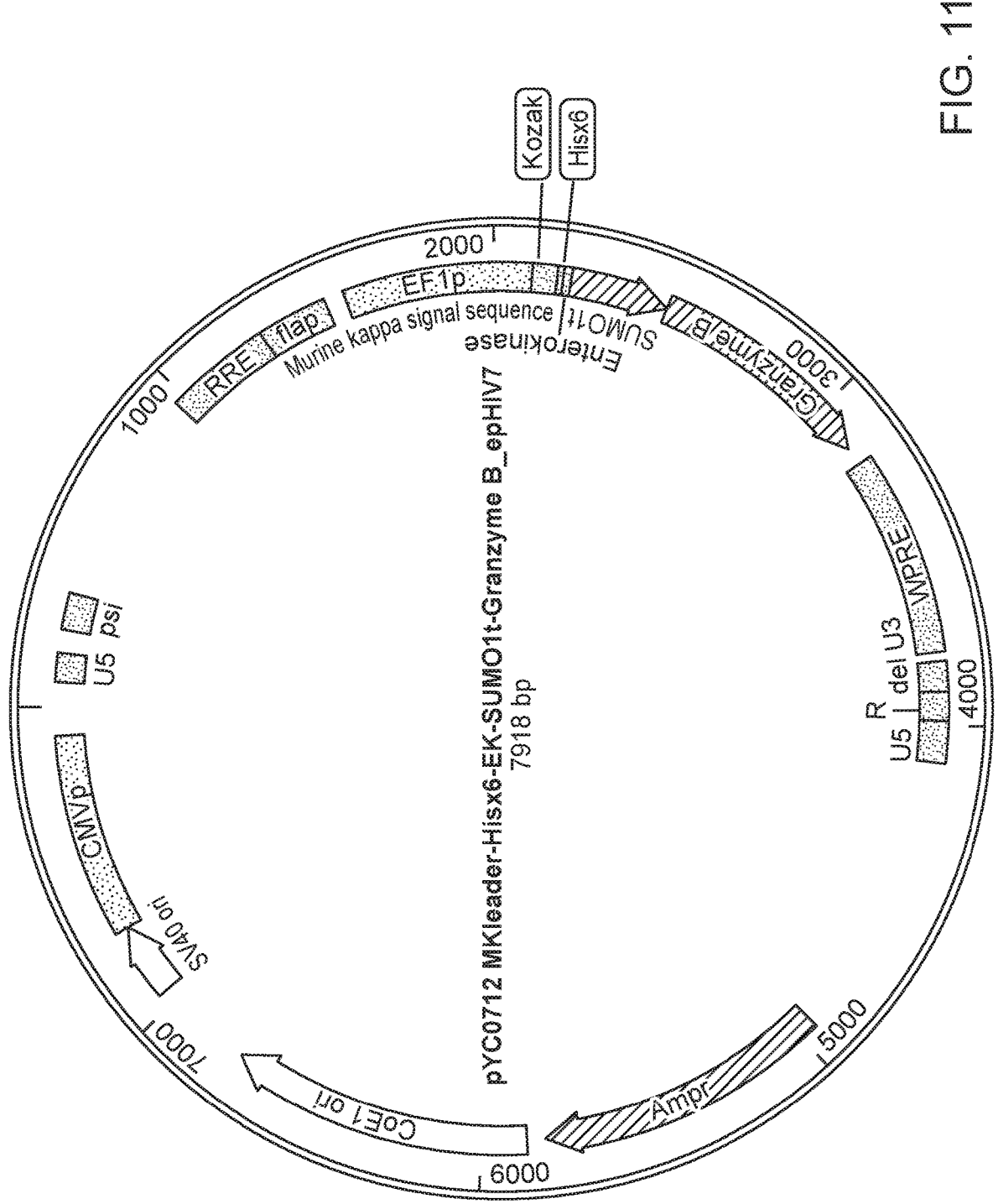

Granzyme B proteins are engineered to be selectively activated by a cytoplasmic protein present in cancer cells targeted for ablation. Examples of the engineered protein include those where an interrogation domain and truncated oncoprotein are fused to the N- and C-terminus of GrB (FIGS. 1 and 9); where an interrogation domain is located internally in a GrB loop and a truncated oncoprotein is fused to the C-terminus (FIGS. 2 and 10); or where the GrB comprises a cleavable moiety fused to the N-terminus (FIGS. 3 and 11). A schematic for activation is shown in FIG. 4.

As shown in FIG. 6, the modified protein is active in the presence of the specific binding partner to the interrogation domain, e.g. where the ID is an EGFP-binding nanobody and the TO is ECFP. The engineered GrB is activated by the presence of EGFP.

Figure 7:
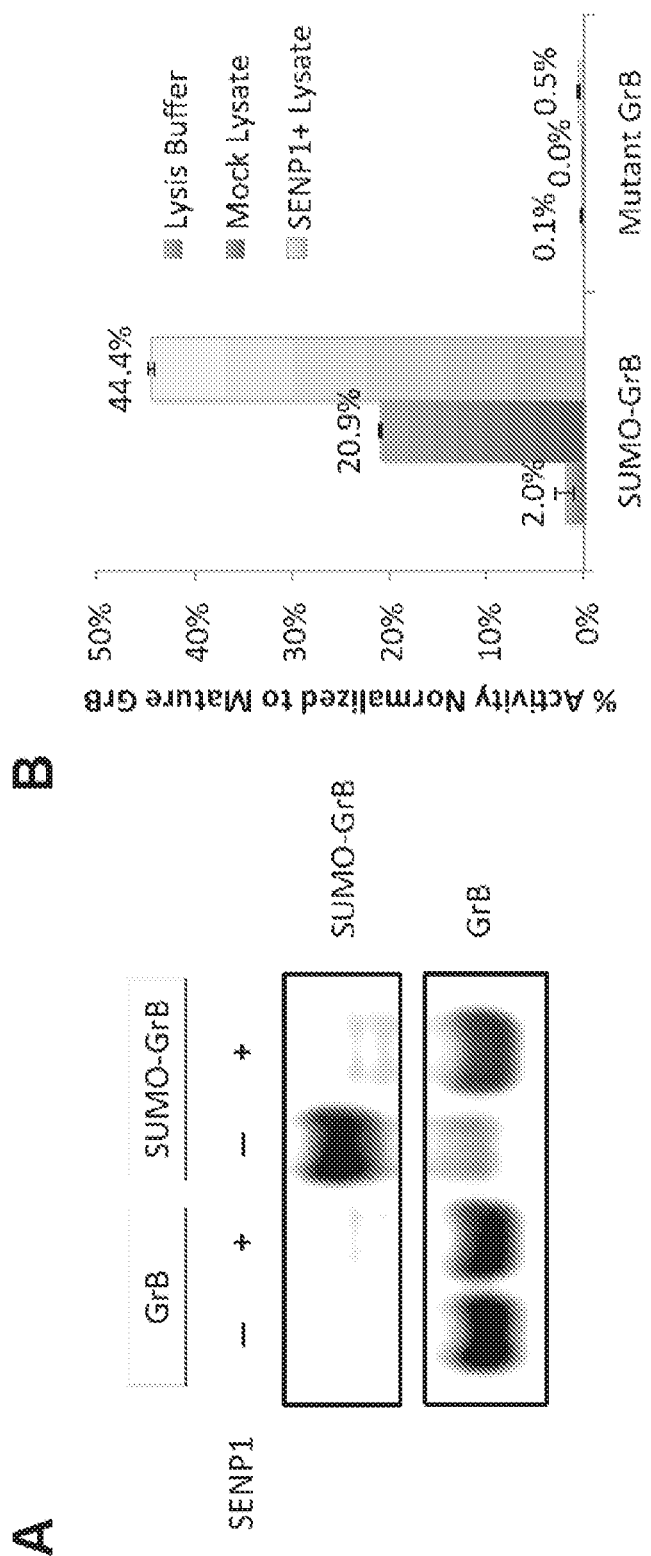
Figure 8:
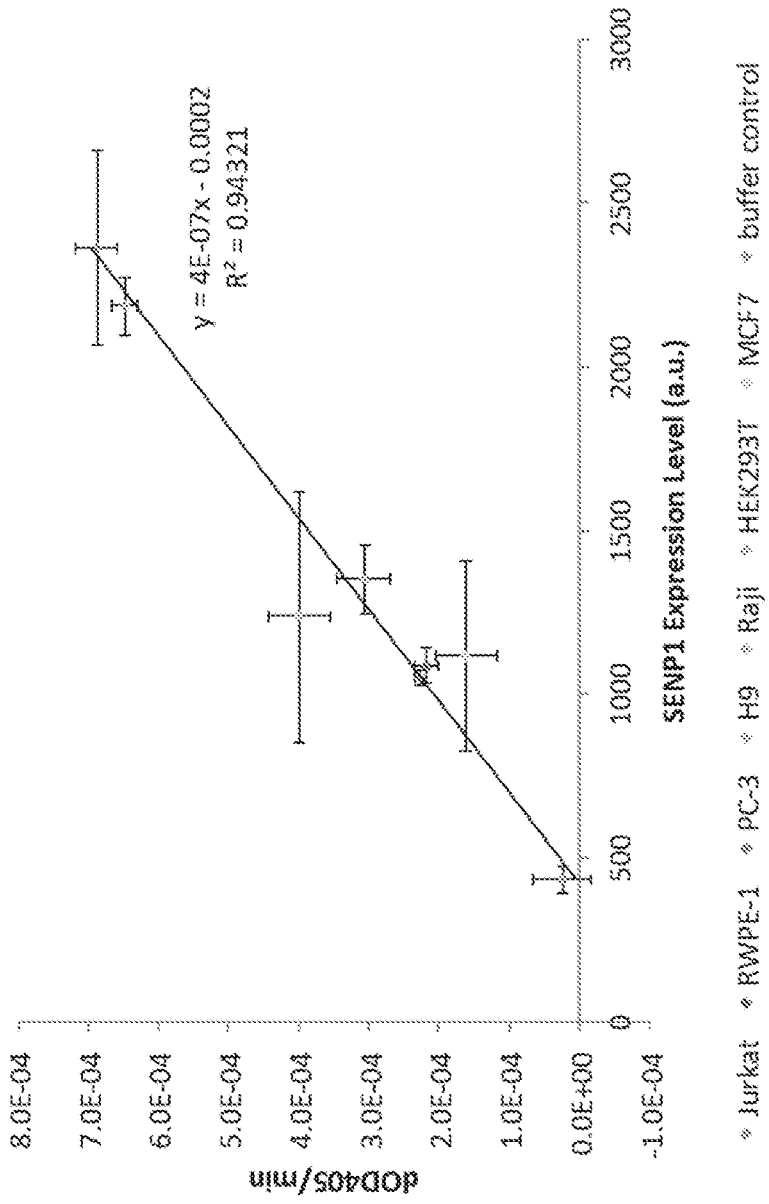

Shown in FIG. 7 is the SENP1-specific processing and in vitro activity of SUMO-modified GrB (as illustrated in FIG. 3). The dose-dependent activation is shown in FIG. 8.

Amino acid sequences for components of the constructs are as follows:

```
Mature granzyme B
                                            (SEQ ID NO: 1)
IIGGHEAKPHSRPYMAYLMIWDQKSLKRCGGFLIQDDFVLTAAHCWGSSI

NVTLGAHNIKEQEPTQQFIPVKRPIPHPAYNPKNFSNDIMLLQLERKAKR

TRAVQPLRLPSNKAQVKPGQTCSVAGWGQTAPLGKHSHTLQEVKMTVQED

RKCESDLRHYYDSTIELCVGDPEIKKTSFKGDSGGPLVCNKVAQGIVSYG

RNNGMPPRACTKVSSFVHWIKKTMKRY

Mature granzyme B up to E188
                                            (SEQ ID NO: 2)
IIGGHEAKPHSRPYMAYLMIWDQKSLKRCGGFLIQDDFVLTAAHCWGSSI

NVTLGAHNIKEQEPTQQFIPVKRPIPHPAYNPKNFSNDIMLLQLERKAKR

TRAVQPLRLPSNKAQVKPGQTCSVAGWGQTAPLGKHSHTLQEVKMTVQED

RKCESDLRHYYDSTIELCVGDPE

Mature granzyme B from I189 onward
                                            (SEQ ID NO: 3)
IKKTSFKGDSGGPLVCNKVAQGIVSYGRNNGMPPRACTKVSSFVHWIKKT
MKRY SUMO-modified granzyme B
                                            (SEQ ID NO: 4)
AATMETDTLLLWVLLLWVPGSTGHHHHHHDDDDKSDQEAKPSTEDLGDKK

EGEYIKLKVIGQDSSEIHFKVKMTTHLKKLKESYCQRQGVPMNSLRFLFE

GQRIADNHTPKELGMEEEDVIEVYQEQTGGIIGGHEAKPHSRPYMAYLMI

WIDQKSLKKGGFLIQDDFVLTAAHCWGSSINVTLGAHNIKEQEPTQQFIP

VKRPIPHPAYNPKNFSNDIMLLQLERKAKRTRAVQPLRLPSNKAQVKPGQ

TCSVAGWGQTAPLGKHSHTLQEVKMTVQEDRKCESDLRHYYDSTIELCVG

DPEIKKTSFKGDSGGPLVCNKVAQGIVSYGRNNGMPPRACTKVSSFVHWI

KKTMKRY

Murine kappa signal sequence
                                            (SEQ ID NO: 5)
METDTLLLWVLLLWVPGSTG Truncated SUMO peptide
                                            (SEQ ID NO: 6)
SDQEAKPSTEDLGDKKEGEYIKLKVIGQDSSEIHFKVKMTTHLKKLKESY
CQRQGVPMNSLRFLFEGQRIADNHTPKELGMEEEDVIEVYQEQTGG Linker 1
                                           (SEQ ID NO: 7)
GSSGSGSTGSGSSGTGSSGTSGTGTS Linker 2
                                            (SEQ ID NO: 8)
GSSTGGGGS Linker 3
                                            (SEQ ID NO: 9)
GSSGSGSSGSGSSG Linker 4
                                           (SEQ ID NO: 10)
GGGGS
```

What is claimed is:

1. A fusion protein comprising GrB and an oncoprotein specific binding partner fused internal to GrB.

2. A T cell comprising a fusion protein, wherein the fusion protein comprises mature Granzyme B (GrB) having a cancer-associated protease cleavage site at the N-terminus of GrB.

3. The T cell of claim 2, wherein the cell is engineered to knock out the endogenous GrB gene.

4. The T cell of claim 2, wherein a secretion signal peptide and a histidine tag are attached to the N-terminus of the fusion protein.

5. The T cell of claim 2, wherein a GrB signal peptide is attached to the N-terminus of the fusion protein.

6. The T cell of claim 2, wherein a secretion peptide is attached to the N-terminus of the modified GrB.

7. The T cell of claim 2, wherein the fusion protein comprises a truncated human small ubiquitin-related modifier 1 (SUMO1) polypeptide fused to the N-terminus of the mature form of GrB.

8. The T cell of claim 2, wherein the cancer-associated protease cleavage site comprises a SENP1 cleavage site.

9. The T cell of claim 2, wherein cleavage of the fusion protein by the protease at the protease cleavage site generates a flush cut.

10. The fusion protein of claim 1, wherein the oncoprotein specific binding partner comprises a nanobody or a scFv.

11. The T cell of claim 2, wherein the T cell expresses the fusion protein.

12. The fusion protein of claim 1, wherein the GrB comprises mature GrB.

* * * * *

SEQUENCE LISTING

<160> NUMBER OF SEQ ID NOS: 10

<210> SEQ ID NO 1
<211> LENGTH: 227
<212> TYPE: PRT
<213> ORGANISM: Homo sapiens

<400> SEQUENCE: 1

Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Gln Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225

<210> SEQ ID NO 2
<211> LENGTH: 173
<212> TYPE: PRT
<213> ORGANISM: Homo sapiens

<400> SEQUENCE: 2

Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Gln Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg

```
                    85                  90                  95
Lys Ala Lys Arg Thr Arg Ala Val Gln Pro Leu Arg Leu Pro Ser Asn
                100                 105                 110
Lys Ala Gln Val Lys Pro Gly Gln Thr Cys Ser Val Ala Gly Trp Gly
                115                 120                 125
Gln Thr Ala Pro Leu Gly Lys His Ser His Thr Leu Gln Glu Val Lys
                130                 135                 140
Met Thr Val Gln Glu Asp Arg Lys Cys Glu Ser Asp Leu Arg His Tyr
145                 150                 155                 160
Tyr Asp Ser Thr Ile Glu Leu Cys Val Gly Asp Pro Glu
                165                 170

<210> SEQ ID NO 3
<211> LENGTH: 54
<212> TYPE: PRT
<213> ORGANISM: Homo sapiens

<400> SEQUENCE: 3

Ile Lys Lys Thr Ser Phe Lys Gly Asp Ser Gly Gly Pro Leu Val Cys
1               5                   10                  15
Asn Lys Val Ala Gln Gly Ile Val Ser Tyr Gly Arg Asn Asn Gly Met
                20                  25                  30
Pro Pro Arg Ala Cys Thr Lys Val Ser Ser Phe Val His Trp Ile Lys
                35                  40                  45
Lys Thr Met Lys Arg Tyr
                50

<210> SEQ ID NO 4
<211> LENGTH: 357
<212> TYPE: PRT
<213> ORGANISM: Homo sapiens

<400> SEQUENCE: 4

Ala Ala Thr Met Glu Thr Asp Thr Leu Leu Leu Trp Val Leu Leu Leu
1               5                   10                  15
Trp Val Pro Gly Ser Thr Gly His His His His His His Asp Asp Asp
                20                  25                  30
Asp Lys Ser Asp Gln Glu Ala Lys Pro Ser Thr Glu Asp Leu Gly Asp
                35                  40                  45
Lys Lys Glu Gly Glu Tyr Ile Lys Leu Lys Val Ile Gly Gln Asp Ser
                50                  55                  60
Ser Glu Ile His Phe Lys Val Lys Met Thr Thr His Leu Lys Lys Leu
65                  70                  75                  80
Lys Glu Ser Tyr Cys Gln Arg Gln Gly Val Pro Met Asn Ser Leu Arg
                85                  90                  95
Phe Leu Phe Glu Gly Gln Arg Ile Ala Asp Asn His Thr Pro Lys Glu
                100                 105                 110
Leu Gly Met Glu Glu Glu Asp Val Ile Glu Val Tyr Gln Glu Gln Thr
                115                 120                 125
Gly Gly Ile Ile Gly Gly His Glu Ala Lys Pro His Ser Arg Pro Tyr
                130                 135                 140
Met Ala Tyr Leu Met Ile Trp Asp Gln Lys Ser Leu Lys Arg Cys Gly
145                 150                 155                 160
Gly Phe Leu Ile Gln Asp Asp Phe Val Leu Thr Ala Ala His Cys Trp
                165                 170                 175
Gly Ser Ser Ile Asn Val Thr Leu Gly Ala His Asn Ile Lys Glu Gln
```

```
                180                 185                 190
Glu Pro Thr Gln Gln Phe Ile Pro Val Lys Arg Pro Ile Pro His Pro
            195                 200                 205

Ala Tyr Asn Pro Lys Asn Phe Ser Asn Asp Ile Met Leu Leu Gln Leu
        210                 215                 220

Glu Arg Lys Ala Lys Arg Thr Arg Ala Val Gln Pro Leu Arg Leu Pro
225                 230                 235                 240

Ser Asn Lys Ala Gln Val Lys Pro Gly Gln Thr Cys Ser Val Ala Gly
                245                 250                 255

Trp Gly Gln Thr Ala Pro Leu Gly Lys His Ser His Thr Leu Gln Glu
            260                 265                 270

Val Lys Met Thr Val Gln Glu Asp Arg Lys Cys Glu Ser Asp Leu Arg
        275                 280                 285

His Tyr Tyr Asp Ser Thr Ile Glu Leu Cys Val Gly Asp Pro Glu Ile
        290                 295                 300

Lys Lys Thr Ser Phe Lys Gly Asp Ser Gly Gly Pro Leu Val Cys Asn
305                 310                 315                 320

Lys Val Ala Gln Gly Ile Val Ser Tyr Gly Arg Asn Asn Gly Met Pro
                325                 330                 335

Pro Arg Ala Cys Thr Lys Val Ser Ser Phe Val His Trp Ile Lys Lys
            340                 345                 350

Thr Met Lys Arg Tyr
            355

<210> SEQ ID NO 5
<211> LENGTH: 20
<212> TYPE: PRT
<213> ORGANISM: Homo sapiens

<400> SEQUENCE: 5

Met Glu Thr Asp Thr Leu Leu Leu Trp Val Leu Leu Leu Trp Val Pro
1               5                   10                  15

Gly Ser Thr Gly
            20

<210> SEQ ID NO 6
<211> LENGTH: 96
<212> TYPE: PRT
<213> ORGANISM: Homo sapiens

<400> SEQUENCE: 6

Ser Asp Gln Glu Ala Lys Pro Ser Thr Glu Asp Leu Gly Asp Lys Lys
1               5                   10                  15

Glu Gly Glu Tyr Ile Lys Leu Lys Val Ile Gly Gln Asp Ser Ser Glu
            20                  25                  30

Ile His Phe Lys Val Lys Met Thr Thr His Leu Lys Lys Leu Lys Glu
        35                  40                  45

Ser Tyr Cys Gln Arg Gln Gly Val Pro Met Asn Ser Leu Arg Phe Leu
    50                  55                  60

Phe Glu Gly Gln Arg Ile Ala Asp Asn His Thr Pro Lys Glu Leu Gly
65                  70                  75                  80

Met Glu Glu Glu Asp Val Ile Glu Val Tyr Gln Glu Gln Thr Gly Gly
                85                  90                  95

<210> SEQ ID NO 7
<211> LENGTH: 26
<212> TYPE: PRT
```

```
<213> ORGANISM: Homo sapiens

<400> SEQUENCE: 7

Gly Ser Ser Gly Ser Gly Ser Thr Gly Ser Gly Ser Ser Gly Thr Gly
1               5                   10                  15

Ser Ser Gly Thr Ser Gly Thr Gly Thr Ser
            20              25

<210> SEQ ID NO 8
<211> LENGTH: 9
<212> TYPE: PRT
<213> ORGANISM: Homo sapiens

<400> SEQUENCE: 8

Gly Ser Ser Thr Gly Gly Gly Gly Ser
1               5

<210> SEQ ID NO 9
<211> LENGTH: 14
<212> TYPE: PRT
<213> ORGANISM: Homo sapiens

<400> SEQUENCE: 9

Gly Ser Ser Gly Ser Gly Ser Ser Gly Ser Gly Ser Ser Gly
1               5                   10

<210> SEQ ID NO 10
<211> LENGTH: 5
<212> TYPE: PRT
<213> ORGANISM: Homo sapiens

<400> SEQUENCE: 10

Gly Gly Gly Gly Ser
1               5
```